United States Patent [19]

Fong et al.

[11] Patent Number: 4,959,187
[45] Date of Patent: Sep. 25, 1990

[54] GLYCOLATE ESTER PERACID PRECURSORS

[75] Inventors: Ronald A. Fong, Modesto; Sheldon N. Lewis, Lafayette; Richard J. Wiersema, Tracy; Alfred G. Zielske, Pleasanton, all of Calif.

[73] Assignee: The Clorox Company, Oakland, Calif.

[21] Appl. No.: 258,226

[22] Filed: Oct. 14, 1988

Related U.S. Application Data

[62] Division of Ser. No. 928,070, Nov. 6, 1986, Pat. No. 4,778,618.

[51] Int. Cl.$^5$ .................. C07C 309/29; C07C 69/78; C07C 409/26
[52] U.S. Cl. ........................... 260/402; 8/110; 8/111; 252/186.23; 252/186.42; 260/404; 260/405; 560/100; 560/106; 560/110; 560/111; 560/130; 560/142; 560/222; 560/250; 560/254; 560/266; 562/2
[58] Field of Search ........... 252/186.23, 186.42; 260/502 R, 402, 404, 405; 560/100, 106, 130, 110, 111, 142, 250, 254, 222, 266; 562/2

[56] References Cited

U.S. PATENT DOCUMENTS

| | | | |
|---|---|---|---|
| 3,960,743 | 6/1976 | Nakagawa et al. | 252/99 |
| 4,221,675 | 9/1980 | Schirmann et al. | 252/186 |
| 4,412,934 | 11/1983 | Chung et al. | 252/186.38 |
| 4,681,592 | 7/1987 | Hardy et al. | 8/111 |

OTHER PUBLICATIONS

Chem. Abs., 70: 10797z, (1969).

*Primary Examiner*—Werren B. Lone
*Assistant Examiner*—Vera C. Clarke
*Attorney, Agent, or Firm*—Joel J. Hayashida; Michael J. Mazza; Stephen M. Westbrook

[57] ABSTRACT

The invention provides novel bleaching compositions comprising peracid precursors with the general structure

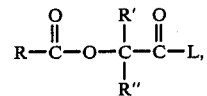

with R, R', R" and L as defined in the specification. Novel peracids and precursors are also herein disclosed. These peracid precursors provide new, proficient and cost-effective compounds for fabric bleaching.

20 Claims, No Drawings

GLYCOLATE ESTER PERACID PRECURSORS

A Division of U.S. Ser. No. 06/928,070, filed Nov. 6, 1986, now U.S. Pat. No. 4,778,618.

Background of the Invention

1. Field of the Invention

This invention relates to a new class of chemical compounds and compositions useful in providing efficient bleaching of textiles over a wide range of washing temperatures, but especially at low temperatures (less than about 50° C.). The present invention provides a new compound for use in detergent bleaches or as laundry additives, said compound having the general formula

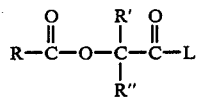

wherein R is $C_{1-20}$ linear or branched alkyl, alkylethoxylated, cycloalkyl, aryl, substituted aryl: R' and R" are independently H, $C_{1-20}$ alkyl, aryl, $C_{1-20}$ alkylaryl, substituted aryl, and $NR_3^{a+}$, wherein $R^a$ is $C_{1-30}$ alkyl; and L is essentially any useful leaving group which can be displaced in a peroxygen bleaching solution by perhydroxide anion. It is most preferred that R' and R" are both H, and thus R'—C—R" is methylene. The alpha hydroxy substituted carbon plus the carbonyl form the glycolate group. When the precursor is combined with a source of hydrogen peroxide, this reaction results in the formation of a peracid, and, under certain circumstances, uniquely to this invention, in the formation of a mixture of peracids. The structure and reactivity of the compounds are unique in that higher yields of peracids can be obtained across a broader pH range and temperature than conventional fatty acid based bleach activators.

2 Brief Description of the Prior Art

Numerous substances have been disclosed in the art as effective bleach activators. British Patent Specification No. 1,147,871, Boldingh et al, describes bleaching and detergent compositions containing an inorganic persalt and acyloxyalkyl or acyl benzene sulfonates. It is claimed that such esters provide improved bleaching temperatures below 70° C. when compared to compositions using the persalt alone.

These activators are represented by the formula:

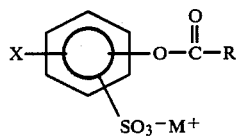

wherein X=branched or straight chain alkyl or acyl radical containing 6-17 carbon atoms; R=H or alkyl radical having 1—7 carbon atoms; and M=an alkali metal, or ammonium radical.

Chung et. al., U.S. Pat. No. 4,412,934, discloses bleaching compositions containing a peroxygen bleaching compound and a bleach activator of the general formula

wherein R is an alkyl group containing from about 5 to about 18 carbon atoms; L is a leaving group, the conjugate acid of which has a $pK_a$ in the range of about 6 to about 13. Chung et al focuses on alkanoyloxy benzene sulfonates, which have been previously disclosed in G.B. No. 864,798, Hampson et al.

Thompson et. al. U.S. Pat. No. 4,483,778, discloses bleach activators of the structure

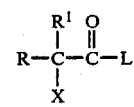

wherein R is $C_{4-14}$ alkyl, R is H or $C_{1-3}$ alkyl, X is —Cl, —OCH$_3$, or —OCH$_2$CH$_3$, and L is a leaving group whose conjugate acid has a $pK_a$ of 4–30. Unlike the apparently crowded alpha carbon in the Thompson et al compound, the present invention has non-hindered enhanced perhydrolytic reactivity. EP No. 166 571, Hardy et. al, discloses the use of a bleach activator compound of the formula $[RX]_mA1$, wherein R is hydrocarbyl, $C_{6-20}$ alkylsubstituted aryl, or alkoxylated hydrocarbyl; X is O, SO$_2$, $N(R^1)_2$, $(R^1)P\rightarrow O$ or $(R^1)N\rightarrow O$, wherein for m=1, A includes

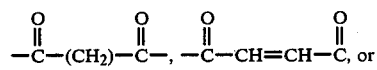

oxybenzene sulfonate.

E.P. 170 368, Burns et al, discloses the use of amide esters of the formula

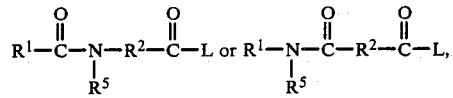

wherein $R^1$ and $R^2$ are alkyl(ene) aryl(ene) or alkylaryl(ene) with 1-14 carbon atoms and $R^5$ is H, an alkyl, or alkylaryl group with 1-10 carbon atoms.

SUMMARY OF THE INVENTION

The present invention provides, in one embodiment, a perhydrolysis system comprising:
(a) a bleaching effective amount of a peracid precursor compound having the general structure

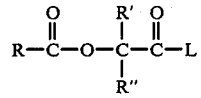

wherein R is $C_1$—$C_{20}$ linear or branched alkyl, alkylethoxylated. cycloalkyl, aryl, substituted aryl; R' and R" are independently H, $C_{1-20}$ alkyl, aryl, $C_{1-20}$ alkylaryl; substituted aryl, and $NR_3^{a+}$, wherein $R^a$ is $C_{1-30}$; and L is essentially any useful leaving group which can be displaced in a peroxygen bleaching solution by perhydroxide anion; and (b) a bleach effective amount of a compound which provides hydrogen peroxide in aqueous media.

The invention further provides a novel peracid having the structure

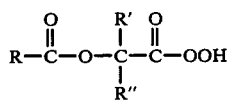

wherein R, R', and R" are as defined above.

The invention also provides novel peracid precursors having the structure

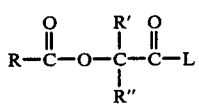

in which L is selected from the group consisting essentially of: phenol derivatives; oxynitrogen groups (amine oxide, hydroxyimide and oxime groups); and carboxylic acids (from mixed esters).

In a further embodiment, the invention provides a bleaching composition comprising:
(a) a bleach effective amount of a compound including the substituent

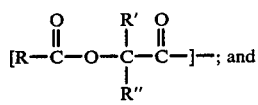

(b) a bleach effective amount of a source of hydrogen peroxide

DETAILED DESCRIPTION OF THE INVENTION

The present invention provides new compounds and compositions useful for low temperature fabric bleaching applications. The compounds of interest to the invention,

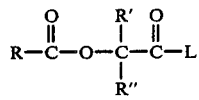

wherein each substituent is as hereinbefore defined, provide several advantages over previously disclosed compositions, for example:

1. Superior Low Temperature Reactivity: Many peracid precursors suffer from low rates of reaction and require exceedingly high temperatures to provide effective bleach. Exemplary of such activators are tetracetyl glycouril (TAGU) and tetraacetyl ethylene diamine (TAED). The precursors of the invention provide effective bleaching at the low temperatures prevalent in U.S. washing conditions (generally, under 100° F.).

2. Higher peracid yields Across a Wider pH Range: Prior peracid precursors have been limited by the fact that pH of wash liquors which are optimal for fabric laundering or bleaching may be inimical to in situ formation of peracids, and vice versa. The present invention is not as affected by this phenomenom.

3. Provides Mixture of Peracids Under Selected Conditions: Depending on the reaction conditions, the precursors of the present invention can beneficially provide more than one type of peracid. At pH 10.5 or greater, hydroperoxide anion is believed to combine with the precursors to form at least two different peracids. As an example, if the inventive precursor is octanoyl glycolate,

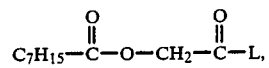

formation of up to three different peracids, may occur:

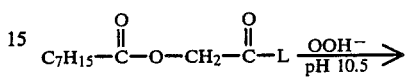

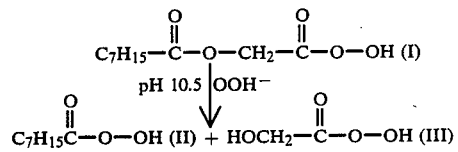

(I) Peroctanoyl glycolic acid (Octanoyloxyperacetic Acid)
(II) Peroctanoic Acid (Percaprylic acid)
(III) Hydroxyperacetic Acid (Perglycolic acid)

The first and third peracids produced, alkanoyloxyperacetic acid and perglycolic acid, are new bleaching compounds.

4. Effectiveness Not Substantially Tied to Molar Ratio of $H_2O_2$ Precursor: In Chung et al, U.S. Pat. No. 4,412,934, it has been alleged that the amount of hydrogen peroxide must exceed the precursor in a molar excess in order to achieve meaningful amounts of peracid. However, the present invention is not so restricted.

The invention also allows the use of less amenable leaving groups previously not possible with conventional fatty acid based esters for hydrogen peroxide activation purposes. The enhanced reactivity of the novel compounds is the result of structural modifications to the acyl group to reduce the pKa of the corresponding carboxylic acid. The change in reactivity has been accomplished via attachment of a more electronegative atom, X, or an electron withdrawing group,

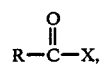

in the structure

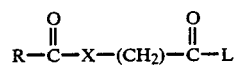

at the alpha-position to the terminal carbonyl group. In the present invention, X=oxygen, and relates to acylglycolic acid esters and derivatives thereof. X, however, could also be another electronegative atom, such as —S—(sulfide).

The base carbonyl is a glycolic acid derivative. The glycolic acid derivatives have been found surprisingly effective in this invention.

Most preferably, when the heteroatom, X is oxygen, and the carbylene group is methylene (R' and R" are both H), the effect of an electronegative substituent alpha to the terminal carbonyl enhances the reactivity of the inventive precursors.

The electronic effect of this modification at the proximal methylene group appears to make the carbonyl group more susceptible to nucleophilic attack by a perhydroxide anion. The resulting enhanced reactivity results in higher peracid yields at low temperatures (e.g., 70° F.), across a broader pH range, and makes the perhydrolysis reaction to generate peracids less susceptible to critical activator to $H_2O_2$ ratios. The following tables illustrate these points:

TABLE I

A. MOLAR RATIO EFFECT

|  | Temp. | Molar[3] Ratio | % Peracid Yield, pH 9.5 |
|---|---|---|---|
| C8-NOBS[1] | 70° | 2/1 | 45 |
|  | 70° | 1/1 | 35 |
| C8-Glycolate[2] | 70° | 2/1 | 85 |
|  | 70° | 1/1 | 80 |

[1]Octanoyloxybenzene sulfonate, peracid activator as described in U.S. Pat. No. 4,412,934.
[2]Octanoyl glycolate (invention)
[3]molar ratio of $H_2O_2$: precursor/activator

TABLE II

B. pH EFFECT

|  | Temp. | Molar[3] Ratio | % Peracid Yield, pH 10.5 | 9.5 | 8.5 |
|---|---|---|---|---|---|
| C8-NOBS[1] | 70° | 2/1 | 79 | 45 | 11 |
| C8-Glycolate[2] | 70° | 2/1 | 90 | 85 | 63 |

[1]Octanoyloxybenzene sulfonate, peracid activator as described in U.S. Pat. No. 4,412,934.
[2]Octanoyl glycolate (invention)
[3]molar ratio of $H_2O_2$: precursor/activator

TABLE III

C. TEMPERATURE EFFECT

|  | Temp. | Molar[3] Ratio | % Peracid Yield, pH 9.5 |
|---|---|---|---|
| C8-NOBS[1] | 70° | 2/1 | 45 |
|  | 100° | 2/1 | 44 |
| C8-Glycolate[2] | 70° | 2/1 | 85 |
|  | 100° | 2/1 | 93 |

[1]Octanoyloxybenzene sulfonate, peracid activator as described in U.S. Pat. No. 4,412,934.
[2]Octanoyl glycolate (invention)
[3]molar ratio of $H_2O_2$: precursor/activator The preferred precursors of the invention are derivatives of glycolic acid, also known as hydroxyacetic acid. Thus, the inventive precursors may be also designated as acyloxyacetic acid esters. A novel chemical property of these acyloxyacetic acid esters is that uniquely at pH's of about 10.5 or higher, as many as three different peracids (I-III, see above, page 5) can be generated. This is advantageous because it would allow bleaching of a wider range of stains.

However, unique to this invention, the subject compounds have added flexibility in that if only the acyloxyperacid is desired for a particular application, this can be achieved by maintaining a $H_2O_2$/ester molar ratio of about 1.0, or by lowering the pH to <10. This flexibility is not available to prior art disclosures, including the acyl amidoacetic esters disclosed in EP No. 170386.

It has been surprisingly found that the second perhydrolysis is highly dependent on the structure of the terminal carbonyl moiety

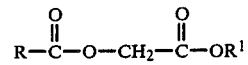

If $R^1 =$ H (i.e., acylglycolic acid), no secondary perhydrolysis occurs.

If $R^1 =$ OH (i.e, alkanoyloxyperacetic or acylperglycolic acid), secondary perhydrolysis occurs and a mixture of peracids is obtained.

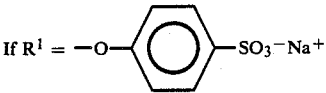

(i.e., acyl glycolic acid, p-phenyl sulfonate ester), the first perhydrolysis occurs at the terminal carbonyl moiety to form the alkanoyloxyperacetic acid, which at pH greater than 10.0 undergoes the secondary perhydrolysis to generate the mixture of peracids.

The advantages of this chemistry is that at pH 10.5, it is feasible to deliver three different peracids (I-III) with differing levels of hydrophilicity and hydrophobicity. It is believed that this mixture of peracids would allow bleaching across a wider range of stains than that possible with conventional bleaching activators.

The enhanced reactivity of the inventive compounds also affords some unique advantages for their use in bleaching compositions. The prior art (Chung, et. al., U.S. Pat. No. 4,412,934,) discloses that specific molar ratios of hydrogen peroxide to bleach activator of greater than about 1.5, preferably 2.0, are critical to obtaining the desired level of peracid needed for effective bleaching. The criticality of the molar ratio was ascribed to a hydrophobic-hydrophobic interaction of the alkyl chain of the acyl group of the peracid and the unreacted activator, which results in formation of diacylperoxides and limits peracid yields. Chung et al, U.S. Pat. No. 4,412,934, stipulates that ratios higher than 1.5 of $H_2O_2$ to activator reduce this problem. The contended novelty of Chung et al's invention is that the enhanced reactivity of the subject compounds allows high peracid yields at molar ratios of $H_2O_2$ to activator of greater than about 1.5.

In the present invention, the non-binding theory is proposed that the electron withdrawing effects of an alpha-substituent make the terminal carbonyl carbon more susceptible to nucleophilic attack by $OOH^-$, and thus excess $OOH^-$ is not required to drive the perhydrolysis reaction to completion. Additionally, it is proposed that by introducing an ester functionality in close proximity to the terminal carbonyl group, sterically or via polarization effects the hydrophobic-hydrophobic interaction is minimized which appears to be responsible for diacylperoxide formation.

Prior art disclosures (Thompon Et. Al. U.S. Pat. No. 4,483,781,) reveal that alpha-chloro and alpha alkoxy esters are contended to be useful as perhydrolysis precursors. The acyloxyacetate esters of the invention, on the other hand, have inherent advantages in that the terminal carbonyl is sterically less crowded and have unique properties which allow delivery of mixtures of peracids.

An additional advantage of this invention is that the second ester functionality significantly modifies the odor of the resulting peracid or carboxylic acid formed. The malodor associated with fatty acid based peracids is well known. The acyloxyacetic acid esters provide an effective solution to the odor problem. However, if it is desirable to execute this chemistry at pH>10, the generation of a mixture of peracids would result in lower odor because of the higher solubility of the in situ generated peracids in highly alkaline media.

The uniqueness of the proposed invention is that the enhanced perhydrolysis reactivity of the subject compounds compared to the fatty acid based esters may allow the use of less amenable leaving groups in the precursor such as hydroxyimides or oxime, and related oxynitrogen groups. Such leaving groups would be impractically slow for perhydrolysis purposes on fatty acid based esters.

In summary, the compounds of the present invention, especially the acyloxyacetic acid esters. Possess significant advantages in reactivity. yields, and bleaching performance over the fatty acid based ester precursors. They generate much less of the malodor associated with fatty peracids, they function over a broader pH range and at low temperatures. At pH greater than 10 and $H_2O_2$/activator molar ratios greater than 1, a mixture of peracids can be obtained. They do not require a critical molar ratio of $H_2O_2$ to activator, and the mixture of peracids formed at pH greater than 10 allow bleaching over a wider range of stains.

The general structure of the invention is

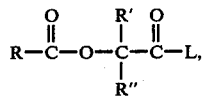

with R, R', R" and L as previously defined.

In one embodiment of the invention is provided:

A bleaching composition comprising:

(a) a peracid precursor having the general structure:

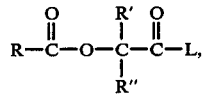

wherein R is $C_{1-20}$ linear or branched alkyl, alkoxylated alkyl, cycloalkyl, aryl, alkylaryl, substituted aryl; R' and R" are independently H, $C_{1-20}$ alkyl, aryl, $C_{1-20}$ alkylaryl, substituted aryl, and $NR_3^{a+}$, wherein $R^a$ is C alkyl; and L is a leaving group; and (b) a bleach-effective amount of a source of hydrogen peroxide.

In the following discussion, certain definitions are utilized:

Peracid precursor is equivalent to bleach activator. Both terms generally relate herein to reactive esters which have a leaving group substituent, which during perhydrolysis, actually cleave off the acyl portion of the ester.

Perhydrolysis is the reaction which occurs when a peracid precursor or activator is combined in a reaction medium (aqueous medium) with an effective amount of a source of hydrogen peroxide.

The leaving group is basically a substituent which is attached via an oxygen bond to the acyl portion of the ester and which can be replaced by a perhydroxide anion (OOH—) during perhydrolysis. The basic reaction is:

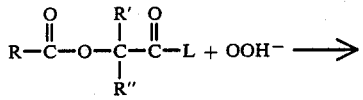

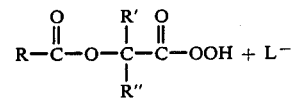

Although further discussion below will elaborate on the unique advantages of the preferred embodiment,

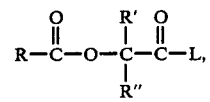

also referred to as a glycolate ester or as an acyloxyglycolate ester, at present, the constituent portions of the ester. i.e., the acyl group and the leaving groups are herein defined.

R is defined as being $C_{1-20}$ linear or branched alkyl, alkoxylated alkyl, cycloalkyl, aryl, substituted aryl or alkylaryl.

It is preferred that R is $C_{1-20}$ alkyl or alkoxylated alkyl. More preferably, R is $C_{1-10}$, and mixtures thereof. R can also be mono-unsaturated or polyunsaturated. If alkoxylated, ethoxy (EO) —(—$OCH_2CH_2$) and propoxy (PO) —(—$OCH_2CH_2CH_2$) groups are preferred, and can be present, per mole of ester, from 1-30 EO or PO groups, and mixtures thereof.

It is especially described for R to be from 4 to 17, most preferably 6 to 12, carbons in the alkyl chain. Such alkyl groups would be surface active and would be desirable when the precursor is used to form surface active peracids for oxidizing fat or oil based soils from substrates at relatively low temperatures.

It is further highly preferred for R to be aryl and $C_{1-20}$ alkylaryl. A different type of bleaching compound results when aromatic groups are introduced onto the ester.

Alkyl groups are generally introduced onto the ester via an acid chloride synthesis discussed further below. Fatty acid chlorides such as hexanoyl chloride, heptanoyl chloride, octanoyl chloride, nonanoyl chloride, decanoyl chloride and the like provide this alkyl moiety. Aromatic groups can be introduced via aromatic acid chlorides (e.g., benzoyl chloride) or aromatic anhydrides (e.g., benzoic acid anhydride).

R' and R" are independently H, $C_{1-20}$ alkyl, aryl, $C_{1-20}$ alkylaryl, substituted aryl, and $NR_3^{a+}$, wherein Ra is $C_{1-30}$ alkyl. When R' and R" are both alkyl, aryl, alkylaryl, substituted alkyl, or mixtures thereof, preferably the total number of carbons of R' +R" does not exceed about 20, more preferably does not- exceed about 18: Alkyl of about 1-4 are preferred. If R' or R" are substituted aryl, substituents include $OH^-$, $SO_3^-$, and $CO_2^-$; R' or R" can be $NR_3^{a+}$($R^a$ is $C_{1-30}$ carbons, and preferably, two of $R^a$ are short chain ($C_{1-4}$) alkyls and one of $R^a$ is a long chain alkyl ($C_{6-24}$) Appropriate positive counterions to include Na+, K+, etc. and appropriate negative counterions include halogen (e.g., $C^-$), OH- —and methosulfate. It is preferred that at least one of R' and R" be H, and most preferably, both (thus forming methylene).

Although applicants have briefly mentioned the importance of the R' and R" alpha, alpha substituents on the carbylene of the acyl group, it is again stressed that the position of various substituents alpha to the proximal carbonyl is very important to this invention.

The leaving group, as discussed above, is basically capable of being displaced by perhydroxide anion in aqueous medium. Unlike prior art precursors, the invention is not limited to leaving groups having particular solubility or reactivity criteria due to the reactiveness of the acyl of the inventive precursor.

Thus, the preferred leaving groups, none of which are meant to limit the invention, include:
(a) phenol derivatives
(b) halides
(c) oxynitrogen leaving groups
(d) carboxylic acid (from a mixed anhydride)

(a) Phenol Derivatives

The phenol derivatives can be generically defined as:

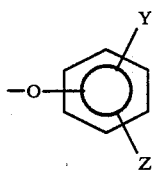

wherein Y and Z are, individually H. $SO_3M$. $CO_2M$, $SO_4M$, OH, halo substituent, $-OR^2$, $R^3$, $NR_3^4 X$, and mixtures thereof, wherein M is an alkali metal or alkaline earth counterion, $R^2$ of the $OR^2$ substituent is $C_{1-20}$ alkyl, $R^3$ is $C_{1-6}$ alkyl, $R^4$ of the $NR_3^4$ substituent is $C_{1-30}$ alkyl, X is a counterion, and Y and Z can be the same or different.

The alkali metal counterions to sulfonate, sulfate or carbonate (all of which are solubilizing groups) include $K^+$, $Li^+$ and most preferably, $Na^+$. The alkaline earth counterions include $Sr^{++}$, $Ca^{++}$, and most preferably, $Mg^{++}$. Ammonium ($NH_4^+$) and other positively charged counterions suitable. The halo substituent can be F, Br or most preferably, Cl. When $-OR^2$, alkoxy, is the substituent on the phenyl ring, $R^2$ is $C_{1-20}$, and the criteria defined for R on the acyl group apply. When $R^3$ is the substituent on the phenyl ring, it is a $C_{1-10}$ alkyl, with preference given to methyl, ethyl, N- and isopropyl, N-, sec- and tertbutyl, which is especially preferred.

When $-NR_3^4 X$, quaternary ammonium, is the substituent, it is preferred that two of $R^4$ be short chain alkyls ($C_{1-4}$, most preferably, methyl) and one of the $R^4$ alkyls be longer chain alkyl (e.g., $C_{8-30}$), with X, a negative counterion, preferably selected from halogen ($Cl^-$, F, $Br^-$, $I^-$), $CH_3SO_4^-$ (methosulfate), $NO_3^-$, or $OH^-$.

Especially preferred are phenol sulfonate leaving groups. A preferred synthesis of phenol sulfonate esters which could be adapted for use herein is disclosed in pending application Ser. No. 915,133, filed Oct. 3, 1986, now Alfred G. Zielske, U.S. Pat. No. 4,735,740, commonly assigned to The Chlorox Company, said application being incorporated herein by reference.

Non-limiting preferred phenol derivatives are:

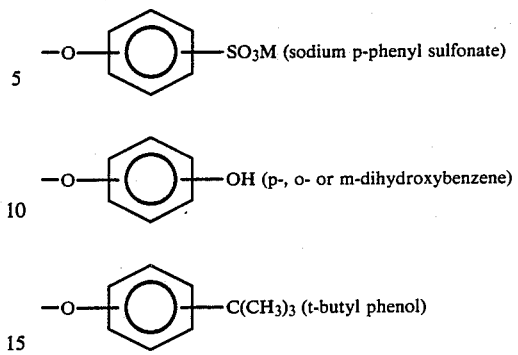

The halide leaving groups are quite reactive and actually are directly obtained as the intermediates in the synthesis of the phenyl sulfonate and t-butylphenol esters. While halides include Br and F. $Cl$ is most preferred. A non-limiting example is:
—Cl (Chloride)

(c) Oxynitrogen

The oxynitrogen leaving groups are especially preferred. In the co-pending application entitled "Acyloxynitrogen Peracid Precursors," inventor Alfred G. Zielske, commonly assigned to The Clorox Company, Oakland, Calif. filed concurrently herewith, Ser. No. 928,065, filed Nov. 6, 1986 incorporated herein by reference, a detailed description of the synthesis of these leaving groups is disclosed. These oxynitrogen leaving groups are generally disclosed as $-ONR^6$, wherein $R^6$ comprises at least one carbon which is singly or doubly bonded directly to N. $-ONR^6$ is more specifically defined as:

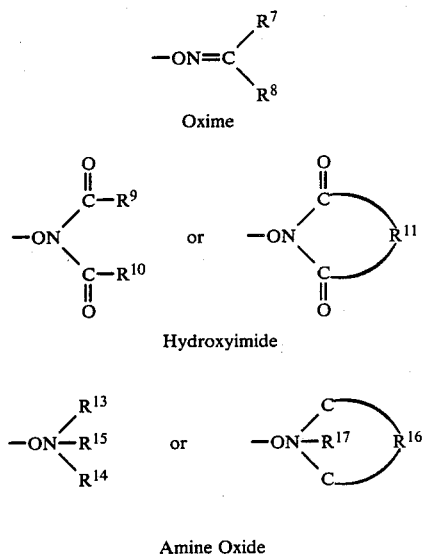

Oxime leaving groups have the structure

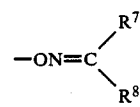

wherein $R^7$ and $R_8$ are individually H, $C_{1-20}$ alkyl, (which can be cycloalkyl, straight or branched chain), aryl, or alkylaryl and at least one of $R^7$ and $R^8$ is not H. Preferably $R^7$ and $R^8$ are the same or different, and range from $C_{1-6}$. Oximes are generally derived from the reaction of hydroxylamine with either aldehydes or ketones.

Non-limiting examples of an oxime leaving group are: (a) oximes of aldehydes (aldoximes), e.g., acetaldoxime, benzaldoxime, propionaldoxime, butylaldoxime, heptaldoxime, hexaldoxime, phenylacetaldoxime, p-tolualdoxime, anisaldoxime, caproaldoxime, valeraldoxime and p-nitrobenzaldoxime; and (b) oximes of ketaones (ketoximes), e.g., acetone oxime (2-propanone oxime), methyl ethyl ketoxime (2-butanone oxime), 2-pentanone oxime, 2-hexanone oxime, 3-hexanone oxime, cyclohexanone oxime, acetophenone oxime, benzophenone oxime, and cyclopentanone oxime.

Particularly preferred oxime leaving groups are:

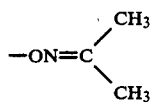 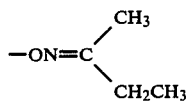

Acetone Oxime     Methylethyl Ketoxime

Hydroxyimide leaving groups comprise:

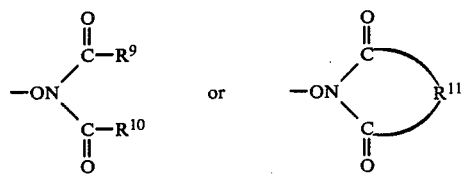

wherein $R^9$ and $R^{10}$ can be the same or different, and are preferably straight chain or branched $C_{1-20}$alkyl, aryl, alkylaryl or mixtures thereof. If alkyl, $R^9$ and $R^{10}$ can be partially unsaturated. It is especially preferred that $R^9$ and $R^{10}$ are straight or branched chain $C_{1-6}$ alkyls, which can be the same or different. $R^{11}$ is preferably $C_{1-20}$ alkyl, aryl or alkylaryl, and completes a heterocycle. $R^{11}$ includes the preferred structure

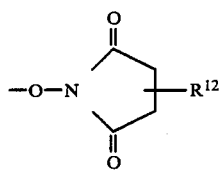

wherein $R^{12}$ can be an aromatic ring fused to the heterocycle, or $C_{1-6}$ alkyl (which itself could be substituted with water solubilizing groups, such as EO, PO, $CO_2^-$ and $SO_3^-$).

These esters of imides can be prepared as described in Greene, *Protective Groups in Organic Synthesis*. p. 183, (incorporated by reference) and are generally the reaction products of acid chlorides and hydroxyimides.

Non-limiting examples of N-hydroxyimide which will provide the hydroxyimide leaving groups of the invention include: N-hydroxysuccinimide, N-hydroxyphthalimide, N-hydroxyglutarimide. N-hydroxynaphthalimide, N-hydroxymaleimide, N-hydroxydiacetylimide and N-hydroxydipropionylimide.

Especially preferred examples of hydroxyimide leaving groups are:

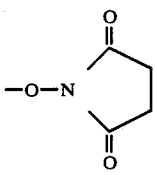 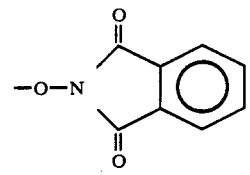

Oxysuccinimide     Oxyphthalimide

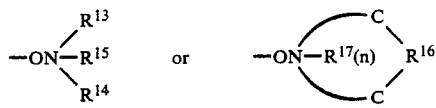

In the first preferred structure for amine oxides, $R^{13}$ and $R^{14}$ can be the same or different, and are preferably $C_{1-20}$ straight or branched chain alkyl, aryl, alkylaryl or mixtures thereof. If alkyl, the substituent could be partially unsaturated. Preferably, $R^{13}$ and $R^{14}$ are $C_{1-4}$ alkyls and can be the same or different. $R^{15}$ is preferably $C_{1-30}$ alkyl, aryl, alkylaryl and mixtures thereof. This $R^{15}$ substituent could also be partially unsaturated. It is most preferred that $R^{13}$ and $R^{14}$ are relatively short chain alkyl groups ($CH_3$ or $CH_2CH_3$) and $R^{15}$ is preferably $C_{1-20}$ alkyl, forming together a tertiary amine oxide.

Further, in the second preferred amine oxide structure, $R^{16}$ can be $C_{1-20}$ alkyl, aryl or alkylaryl, and completes a heterocycle. $R^{16}$ preferably completes an aromatic heterocycle of 5 carbon atoms and can be $C_{1-6}$ alkyl or aryl substituted. $R^{17}$ is preferably nothing, $C_{1-30}$ alkyl, aryl, alkylaryl or mixtures thereof. $R^{17}$ is more preferably $C_{1-20}$ alkyl if $R^{11}$ completes an aliphatic heterocycle. If $R^{16}$ completes an aromatic heterocycle, $R^{17}$ is nothing.

Non-limiting examples of amine oxides suitable for use as leaving groups herein can be derived from: Pyridine N-oxide, trimethylamine N-oxide, 4-phenyl pyridine N-oxide, decyldimethylamine N-oxide, dodecyldimethylamine N-oxide, tetradecyldimethylamine N-oxide, hexadecyldimethylamine N-oxide, octyldimethylamine N-oxide, di(decyl)methylamine N-oxide, di(dodecyl)methylamine N-oxide, di(tetradecyl)methylamine N-oxide, 4-picoline N-oxide, 3-picoline N-oxide and 2-picoline N-oxide.

Especially preferred amine oxide leaving groups include:

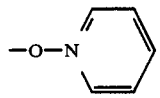 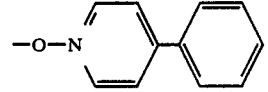

Pyridinium N-oxide     Phenylpyridinium N-oxide (d) Carboxylic Acids from Mixed Anhydrides Carboxylic acid leaving groups have the structure

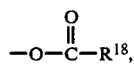

wherein $R^{18}$ is $C_{1-10}$ alkyl, preferably $C_{1-4}$ alkyl, most preferably either $CH_3$ or $CH_2CH_3$ and mixtures thereof.

When $R^{18}$ is $C_1$ and above, it is believed that the leaving groups will form carboxylic acids upon perhydrolytic conditions. Thus, when $R^{18}$ is $CH_3$, acetic acid would be the leaving group; when $CH_2CH_3$, propionic acid would be the leaving group, and so on. However, the foregoing theory is non-binding and offers only one explanation for what may be a very complicated reaction.

Non-limiting examples of mixed anhydride esters include:

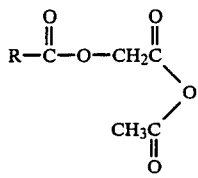

Alkanoyloxy acetic/acetic acid mixed anhydride;

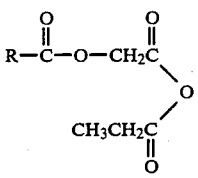

Alkanoyloxyacetic/Propionic acid mixed anhydride.

A preferred synthesis of these mixed anhydrides appears in the EXPERIMENTAL section below.

The Peracid Alkanoyloxyperacetic Acid (I)

In another especially preferred embodiment of the invention, is provided a new organic peracid, which will be named alkanoyloxyperacetic acid (but, it R is aryl, the peracid is benzoyloxyperacetic acid; and, if R is alkylaryl, the peracid is alkylbenzoyloxy peracetic acid), of the structure.

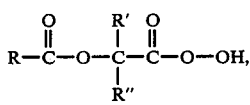

wherein R is defined, as for the precursor, as $C_{1-20}$ linear or branched alkyl, alkoxylated alkyl, cycloalkyl, aryl, alkylaryl, substituted aryl and R' and R" are independently H, $C_{1-20}$ alkyl, aryl, $C_{1-20}$ alkylaryl, substituted aryl, and $NR_3^{a+}$, wherein $R^a$ is $C_{1-30}$ alkyl.

The peracid is generated in situ when the inventive precursor

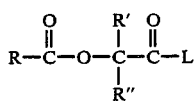

is placed in aqueous solution with a source of hydrogen peroxide which gives rise to perhydroxide anions.

The novel peracid could be synthesized separately, but, because it is fairly unstable—in fact, unless stabilized by exothermic control agents or the like, it might be somewhat explosive -- it is best to generate the compound in situ. This has the added advantage of freeing the synthetic chemist from having to isolate the peracid, to purify it and, of course, to stabilize it.

The peracid is quite unique since, depending on pH (e.g., greater than about 10), the peracid will itself undergo secondary perhydrolysis to give rise to up to potentially two other peracids, namely, the peracid corresponding to the moiety R (II) and perhydroxyacetic acid (III).

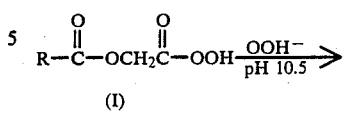

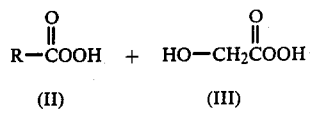

Beneficially, since up to three different peracids potentially capable of attacking different substrates (stains) can be generated, the inventive peracid offers advantages over prior art peracids. For example, EP 68 547 calls for a mixture of separately synthesized hydrophobic, hydrophilic and hydrotropic peracids for allegedly improved textile bleaching. The new peracid, alkanoyloxyperacetic acid will, under certain conditions, provide the three separate peracids from a single compound. or $C_{1-20}$ alkyl, more preferably $C_{4-17}$ alkyl, and most preferably $C_{6-12}$ alkyl. When R is alkyl between $C_{4-17}$, most preferably $C_{6-12}$ alkyl, surface active peracids result, which would appear to have greater oil—and grease based soil removal potential at lower wash temperatures.

Non-limiting examples include:

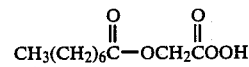

Octanoyloxyperacetic Acid

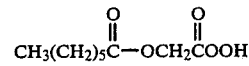

Hexanoyloxyperacetic Acid

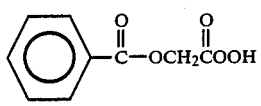

Benzoyloxyperacetic Acid

The above peracids can include other substituents, for instance, the R group can be ethoxylated or propoxylated. Electronegative groups, such as halide, can be added to the alkyl chain, or on the phenyl ring.

A singularly important embodiment of this novel peracid is to stabilize the same, by neutralizing the peracid with either (preferably) an alkaline earth or alkali metal hydroxide, to give rise to the alkaline earth and alkali metal salts of the peracid. respectively:

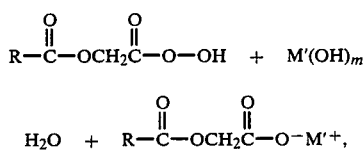

where M' is an alkali metal or alkaline earth salt and m=1 or 2.

Non limiting examples of such alkali metals include monovalent cations, Na+, Li+ and K+. Non-limiting alkaline earth metals would be divalent cations $Ca^{++}$, $Sr^{++}$ and, most preferably. $Mg^{++}$.

The Peracid Perglycolic Acid (III)

In yet another especially preferred embodiment of the invention, is provided a new organic peracid, which will be named perglycolic acid or hydroxyperacetic acid. It has the structure:

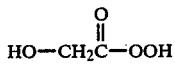

The peracid is generated in situ when the inventive precursor

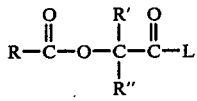

is placed in aqueous solution with a source of hydrogen peroxide which gives rise to perhydroxide anions, at a pH of greater than about 10.

This inventive peracid has the more general structure

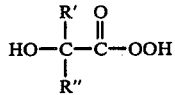

In the above structure. R' and R'' are the substituents previously defined, although, again, it is most preferred for R' and R'' both to be hydrogen.

The novel peracid could be synthesized separately, but, because it is fairly unstable—in fact, unless stabilized by exothermic control agents or the like, it might be somewhat explosive—it is best to generate the compound in situ. This has the added advantage of freeing the synthetic chemist from having to isolate the peracid, to purify it and, of course, to stabilize it.

The peracid is quite unique since, depending on pH (e.g.. greater than about 10). it is a product of the secondary perhydrolysis of the other novel peracid, alkanoyloxyperacetic acid, as described above on page 22, lines 1.5. As in the case of the other novel peracid, it may be desirable to obtain the alkali metal or alkaline earth salt of hydroxyperacetic acid in order to stabilize the same. The same salts as described for the prior, novel peracid would be applicable.

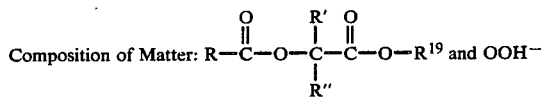

In yet one more preferred embodiment of the invention, is provided
a bleaching composition comprising:
(a) a compound with the structure

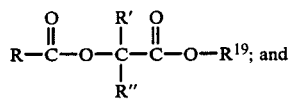

(b) a bleach effective amount of a source of hydrogen peroxide, wherein R is, as previously defined, as $C_{1-20}$ linear or branched alkyl, alkoxylated alkyl, cycloalkyl, aryl, alkylaryl, substituted aryl, and R' and R'' are independently H. $C_{1-20}$ alkyl, aryl. $C_{1-20}$ alkylaryl, substituted aryl, and $NRa+$, wherein $R^a$ is $C_{1-30}$ alkyl;

said composition providing about 0.5 to 100 ppm A.O. in aqueous media.

in the above structure completes an alkoxy ester.

$R^{19}$ is

The alkoxy groups have the structures $-O-R^{19}$. $R^{19}$ is preferably $C_{1-20}$ alkyl, although the same criteria for the R of the acyl group apply. $R^{19}$ is especially preferred as $C_{1-10}$, for example, preferably wherein $R^{19}$ forms the methyl, ethyl, propyl and butyl esters of alkanoyloxyacetic acid. Non-limiting examples of these alkoxy groups are:

$-O-CH_3$ (methyl ester)
$-O-CH_2CH_3$ (ethyl ester)
$-O-CH_2CH_2CH_3$ (n-propyl ester)

In order to enhance the solubility of these compounds, it is preferred to add hydroxyl (—OH) groups to the alkoxy substituent, $-R^{19}$. Thus, preferred alkoxy esters would be polyhydroxylated.

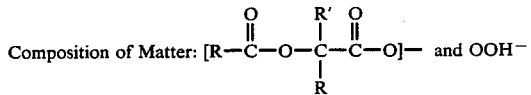

In still one further especially preferred embodiment of the invention is provided:
a bleaching composition comprising:
(a) a compound which includes the substituent

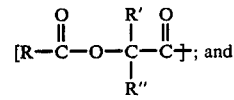

(b) a bleach effective amount of a source of hydrogen peroxide, wherein R is, as previously defined, as $C_{1-20}$ linear or branched alkyl, alkoxylated alkyl, cycloalkyl, aryl, alkylaryl, substituted aryl and n is an integer from 1 to 6. most preferably 1 to 3;

said composition providing about 0.5 to 100 ppm A. O. in aqueous media.

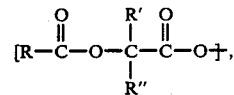

(when R' and R'' are both hydrogen) will be present in a number of different compounds and the only real proviso for excluding any compound from this definition would be that the particular compound does not generate peracid A.O. in aqueous media. All of the disclosed precursors and peracids herein would fit the definition of this composition of matter.

Delivery Systems

The precursors can be incorporated into a liquid or solid matrix for use in liquid or solid detergent bleaches by dissolving into an appropriate solvent or surfactant or by dispersing onto a substrate material, such as an inert salt (e.g, NaCl, $Na_2SO_4$) or other solid substrate, such as zeolites, sodium borate, or molecular sieves. Examples of appropriate solvents include acetone, non-nucleophilic alcohols, ethers or hydrocarbons. Other more water-dispersible or-miscible solvents may be considered. As an example of affixation to a substrate material, the precursors of the present invention could be incorporated onto a non-particulate substrate such as disclosed in published European Patent Application EP No. 98 129. whose disclosure is incorporated herein by reference.

While it has been disclosed by applicants that substituting solubilizing groups may improve the solubility and enhance the reactivity of these precursors, an alternate mode and preferred embodiment is to combine the precursors with a surfactant.

For example, the inventive precursors with oxynitrogen leaving groups are apparently not as soluble in aqueous media as compared to phenyl sulfonates. Other precursors may be similarly somewhat less soluble than phenyl sulfonate esters. Thus, a preferred embodiment of the invention is to combine the precursors with a surfactant. It is particularly preferred to coat these precursors with a nonionic or anionic surfactant that is solid at room temperature and melts at above about 40° C. A melt of surfactant may be simply admixed with peracid precursor, cooled and chopped into granules. Exemplary surfactants for such use are illustrated in Table IV below:

TABLE IV

| Commercial Name | m.p. | Type | Supplier |
|---|---|---|---|
| Pluronic F-98 | 55° C. | Nonionic | BASF Wyandotte |
| Neodol 25-30 | 47° C. | Nonionic | Shell Chemical |
| Neodol 25-60 | 53° C. | Nonionic | Shell Chemical |
| Tergitol-S-30 | 41° C. | Nonionic | Union Carbide |
| Tergitol-S-40 | 45° C. | Nonionic | Union Carbide |
| Pluronic 10R8 | 46° C. | Nonionic | BASF Wyandotte |
| Pluronic 17R8 | 53° C. | Nonionic | BASF Wyandotte |
| Tetronic 90R8 | 47° C. | Nonionic | BASF Wyandotte |
| Amidox C5 | 55° C. | Nonionic | Stepan |

The precursors, whether coated with the surfactants with melting completion temperatures above about 40° C. or not so coated, could also be admixed with other surfactants to provide, depending on formulation, either bleach additive or detergent compositions.

Particularly effective surfactants appear to be nonionic surfactants. Preferred surfactants of use include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0-10 moles of ethylene oxide and about 1 to 10 moles of propylene oxide per mole of alcohol; linear and branched alkylphenoxy (polyethoxy) alcohols, otherwise known as ethoxylate alkylphenols, with an average chain length of 8 to 16 carbon atoms and averaging 1.5 to 0 moles of ethylene oxide per mole of alcohol; and mixtures thereof. Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers of propylene oxide and ethylene oxide with propoxylated ethylene diamine. Also included are such semi-polar nonionic surfactants like amine oxides, phosphine oxides, sulfoxides, and their ethoxylated derivatives.

Anionic surfactants may also be suitable. Examples of such anionic surfactants may include the ammonium, substituted ammonium (e.g., mono-di-, and triethanolammonium). alkali metal and alkaline earth metal salts of $C_6$-$C_{20}$ fatty acids and rosin acids, linear and branched alkyl benzene sulfonates, alkyl sulfates, alkyl ether sulfates, alkane sulfonates, olefin sulfonates, hydroxyalkane sulfonates, fatty acid monoglyceride sulfates, alkyl glyceryl ether sulfates, acyl sarcosinates and acyl N-methyltaurides.

Suitable cationic surfactants may include the quaternary ammonium compounds in which typically one of the groups linked to the nitrogen atom is a $C_{12}$-$C_{18}$ alkyl group and the other three groups are short chained alkyl groups which may bear inert substituents such as phenyl groups.

Further, suitable amphoteric and zwitterionic surfactants which contain an anionic water-solubilizing group, a cationic group and a hydrophobic organic group may include amino carboxylic acids and their salts, amino dicarboxylic acids and their salts, alkylbetaines, alkyl aminopropylbetaines, sulfobetaines, alkyl imidazolinium derivatives certain quaternary ammonium compounds, certain quaternary phosphonium compounds and certain tertiary sulfonium compounds. Other examples of potentially suitable zwitterionic surfactants can be found described in Jones, U.S. 4,005,029, at columns 11-15, which are incorporated herein by reference.

Further examples of anionic, nonionic, cationic and amphoteric surfactants which may be suitable for use in this invention are depicted in Kirk Othmer, *Encyclopedia of Chemical Technology*, Third Edition, Volume 22, pages 347-387, and *McCutcheon's Detergents and Emulsifiers*, North American Edition, 1983, which are incorporated herein by reference.

As mentioned hereinabove, other common detergent adjuncts may be added if a bleach or detergent bleach product is desired. If, for example, a dry bleach composition is desired, the following ranges (weight %) appear practicable:

| | |
|---|---|
| 0.5–50.0% | Hydrogen Peroxide Source |
| 0.05–25.0% | Precursor |
| 1.0–50.0% | Surfactant |
| 1.0–50.0% | Buffer |
| 5.0–99.9% | Filler, stabilizers, dyes, Fragrances, brighteners, etc. |

The hydrogen peroxide source may be selected from the alkali metal salts of percarbonate, perborate, persilicate and hydrogen peroxide adducts and hydrogen peroxide. Most preferred are sodium percarbonate, sodium perborate mono-and tetrahydrate, and hydrogen peroxide. Other peroxygen sources may be possible, such as monopersulfates and monoperphosphates. In liquid applications, liquid hydrogen peroxide solutions are preferred, but the precursor may need to be kept separate therefrom prior to combination in aqueous solution to prevent premature decomposition.

The range of peroxide to peracid precursor is preferably determined as a molar ratio of peroxide to precursor. Thus, the range of peroxide to each precursor is a molar ratio of from about 0.5 to 10:1. more preferably about 1:1 to 5:1 and most preferably about 1:1 to 2:1. It is preferred that this peracid precursor/peroxide composition provide preferably about 0.5 to 100 ppm A.O.

and most preferably about 1 to 50 ppm A.O. and most preferably

A description of, and explanation of, A.O. measurement is found in the article of Sheldon N. Lewis. "Peracid and Peroxide Oxidations," In: *Oxidation.* 1969, pp. 213-258, which are incorporated herein by reference. Determination of the peracid can be ascertained by the analytical techniques taught in *Organic Peracids.* (Ed. by D. Swern), Vol. 1. pp. 501 et sec. (Ch.7) (1970), incorporated here by reference.

An example of a practical execution of a liquid delivery system is to dispense separately metered amounts of the precursor (in some non-reactive fluid medium) and liquid hydrogen peroxide in a container such as described in Beacham et al, U.S. Pat. No. 4,585.150. commonly assigned to The Clorox Company, and incorporated herein by reference.

The buffer may be selected from sodium carbonate, sodium bicarbonate, sodium borate, sodium silicate. Phosphoric acid salts, and other alkali metal/alkaline earth metal salts known to those skilled in the art. Organic buffers, such as succinates, maleates and acetates may also be suitable for use. It appears preferable to have sufficient buffer to attain an alkaline pH. i.e., above at least about 7.0. Also, as further discussed below, it is especially advantageous to have an amount of buffer sufficient to maintain a pH of about 10.5.

The filler material, which, in a detergent bleach application, may actually constitute the major constituent, by weight, of the detergent bleach, is usually sodium sulfate. Sodium chloride is another potential filler. Dyes include anthraquinone and similar blue dyes. Pigments, such as ultramarine blue (UMB), may also be used, and can have a bluing effect by depositing on fabrics washed with a detergent bleach containing UMB. Monastral colorants are also possible for inclusion. Brighteners, such as stilbene, styrene and styrylnapthalene brighteners (fluorescent whitening agents), may be included. Fragrances used for esthetic purposes are commercially available from Norda, International Flavors and Fragrances and Givaudon. Stabilizers include hydrated salts, such as magnesium sulfate, and boric acid.

In one of the preferred embodiments in which a glycolate ester compound such as in Example III below is the precursor, a preferred bleach composition has the following ingredients:

| | |
|---|---|
| 15.6% | Sodium Perborate Tetrahydrate |
| 19.0% | Octanoyl glycolate, p-phenyl sulfonate |
| 7.0% | Nonionic Surfactant |
| 15.0% | Sodium Carbonate |
| 43.4% | Sodium Sulfate |
| 100.0% | |

In another one of the preferred embodiments, in which another glycolate ester compound such as in Example VIII below is the precursor, a preferred bleach composition has the following ingredients:

| | |
|---|---|
| 15.5% | Sodium Perborate Tetrahydrate |
| 16.8% | Octanoyloxy acetic acid, t-butyl phenol ester |
| 7.0% | Nonionic Surfactant |
| 15.0% | Sodium Carbonate |
| 45.7% | Sodium Sulfate |
| 100.0% | |

Other peroxygen sources, such as sodium perborate monohydrate or sodium percarbonate are suitable. If a more detergent-type product is desired, the amount of filler can be increased and the precursor halved or further decreased.

The EXPERIMENTAL section follows hereto. Examples I through XVI depict in detail the syntheses of various inventive precursors. Example XVII demonstrates the excellent perhydrolysis of these inventive precursors.

EXPERIMENTAL

In Examples I through III and IV through VI, the following synthesis route for the synthesis of p-phenylsulfonate esters of alkanoyloxyacetic acid is followed:

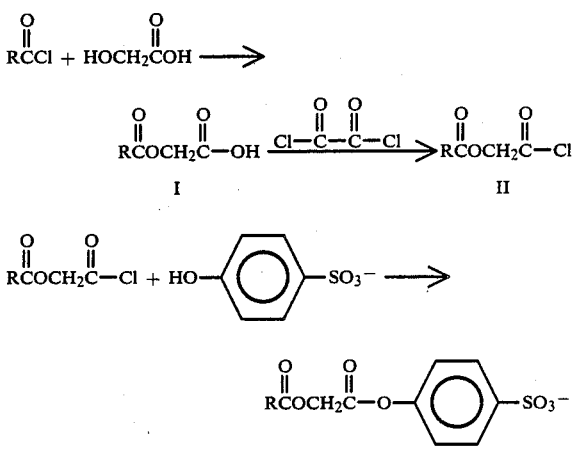

EXAMPLE I

Synthesis of Octanoyloxyacetic acid preparation

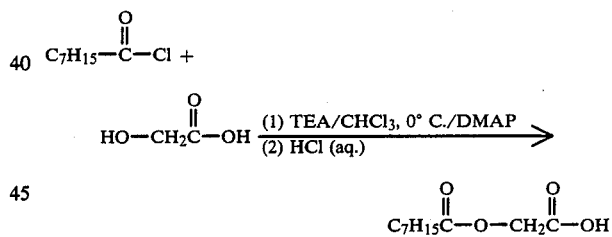

Procedure: A 1 liter, 2 neck round bottom flask was charged with 110.7g (1.46 moles) glycolic acid (Kodak, 97%), 294 g (2.91 moles) triethylamine (TEA, Aldrich 99%), 2.0 g 4-dimethylamino dine (DMAP, 0.16 mole) and 200 ml CHCl$_3$. Dissolution was obtained by mechanical stirring while cooling to 3-4° C. on an ice water bath (an exothermic reaction occurred upon mixing). 0.237g (1.46 mole) octanoyl chloride (Aldrich 99%) was added dropwise via additional funnel over one- and one half hours, during which time a heavy precipitate (triethylamine hydrochloride) formed. The reaction was stirred an additional one-and one half hours. The solids were filtered off (wt. approx. 190 g); and the supernatant (CHCl$_3$) was washed with: 2×500 ml 6% (aq) HCl, 1×500ml water, and 1×500 ml saturated NaCl$_{(aq)}$. The chloroform layer was dried over MgSO$_4$, filtered and rotary evaporated to an oil (extract I) (wt=248 g).

The filtered triethylamine hydrochloride was extracted with 500 ml diethyl ether, which in turn was washed with 250ml 6% MCl, and 250 ml saturated NaCl, dried over MgSO$_4$, filtered and rotary evaporated to an oil (Extract II).

Extracted oils I and II were combined and recrystallized from ml petroleum ether (−20° C.). The crystalline product was isolated by filtration and dried in vacuo. (wt.=130 g) (mp 44-46° C.; approximate % purity, 90 %; Isolated yield=40 %.

The $^{13}$C-NMR (CDCl$_3$, ppm downfield from TMS) showed only absorptions expected for the product. Using the numbering system shown, these assignments were made:

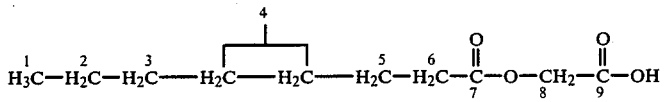

C$_1$(13.7), C$_2$(22.3), C$_3$(24.5), C$_4$(28.7), C$_5$(31.4), C$_6$(33.4), C$_7$(173.1), C$_8$(59.9), and C$_9$(173).

EXAMPLE II

Synthesis of Octanoyloxy acetyl chloride

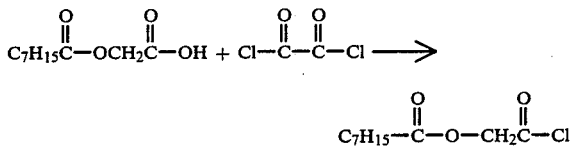

Procedure: 101.1 g (0.5 mole) octanoyloxyacetic acid and 83 g (0.65 mole) oxalyl chloride are combined in a 1 liter round bottom flask with a magnetic stir bar and a CaSO$_4$ drying tube (note: a little hexane or petroleum ether can be added if the solid does not completely dissolve). The reaction is stirred at room temperature while rapid gas evolution is noted, then gradually heated to 40-50° C. for 1 hour (note: the reaction can also be run at room temperature overnight with the advantage that it remains colorless). The slightly yellow solution is then heated to 60-70° C. under aspirator pressure for 1 to 1½ hours to remove excess oxalyl chloride. After cooling to room temperature the oil is diluted with 400 ml petroleum ether (bp 30-60° C.) and extracted with 3×200 ml ice water (caution: gas evolution can be vigorous). The organic layer is dried over MgSO$_4$, filtered and rotovapped to a clear straw colored oil, weight=11.57 g (111.4 g theoretical). IR showed no acid—OH stretch and two carbonyls at 1812 cm$^{-1}$ and at 1755 cm$^{-1}$.

EXAMPLE III

Synthesis of Octanoyloxy acetic acid, phenyl sulfonate ester

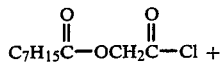

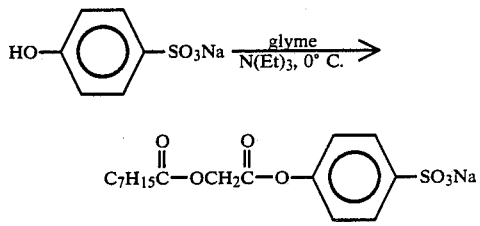

Procedure: 17.3 g (0.079 mole) octanoyloxyacetyl chloride and 17.0 g (0.087 mole) sodium phenol sulfonate (dried at 120° C. in vacuo for 16 hours) were combined in a 250 ml round bottom flask with a magnetic stir bar. 30 ml of ethylene glycol-dimethyl ether (glyme) was added, and the slurry stirred with cooling in an ice-water bath. 7.8 g (0.077 mole) triethyl amine was placed in an addition funnel equipped with a CaSO$_4$ drying tube and this was added dropwise to the above slurry over ½ hour becomes very thick during this time and more glyme (or ethyl ether) can be added at this time to allow efficient stirring. The reaction was stirred for two hours at room temperature, diluted with ethyl ether and stirred 1 hour more. The reaction was filtered on a coarse fritted funnel washed with several portions of ethyl ether, suction-dried for 1 hour and then dried in vacuo at room temperature.

Weight of product: 39g (theoretical wt 42.1 g). This material can be recrystallized from 60/40 (vol/vol) isopropanol/water in an approximate 3 to 4:1 (wt/wt) ratio of solvent to ester reaction mixture to give an approximate 45-60% yield of ester (95 % in purity).

The $^{13}$C-NMR (D$_2$O, ppm downfield from TMS) showed only absorptions expected for the product. Using the numbering system shown, these assignments were made:

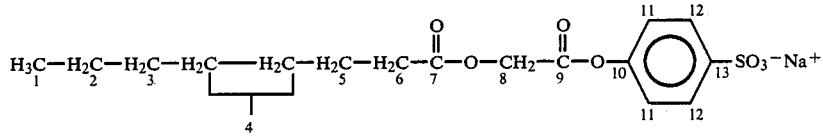

C$_1$(15.9), C$_2$(24.7), C$_3$(27.0), C$_4$(31.0/31.2), C$_5$(33.9), C$_6$(35.9), C$_7$(175.9), C$_8$(63.3), C$_9$(169.7), C$_{10}$(153.9), C$_{11}$(123.8), C$_{12}$(130.0) and C$_{13}$(144.4).

EXAMPLE IV

Synthesis of Hexanoyloxyacetic Acid $$\text{C}_5\text{H}_{11}\overset{\text{O}}{\overset{\|}{\text{C}}}\text{—Cl} + \text{HOCH}_2\overset{\text{O}}{\overset{\|}{\text{C}}}\text{—OH} \xrightarrow[\text{dimethylaminopyridine}]{\text{triethylamine}}$$

$$\text{C}_5\text{H}_{11}\overset{\text{O}}{\overset{\|}{\text{C}}}\text{—OCH}_2\overset{\text{O}}{\overset{\|}{\text{C}}}\text{—OH}$$

25.0 g (0.329 m) of glycolic acid (m.pt. 78-80° C.) 66 g (0.66 m) of triethylamine, and 2.0 g (0.016m) of 4- dimethylaminopyridine were dissolved in 200 ml chloroform in a one liter round bottom flask fitted with a mechanical stirrer and an addition funnel. The solution was cooled to about 5° C. with an ice water bath, and 45.6g (0.329 m) of n-hexanoyl chloride was added dropwise via the addition funnel over one hour. The resulting slurry was stirred for two hours at 0-5° C. after which time the salts were filtered off and the filtrate washed with 1×200 ml of 10%HCl and 1×200 ml saturated sodium chloride. The organic phase was dried over 50 g $Na_2SO_4$, filtered, and the $CHCl_3$ solvent removed via rotary vacuum evaporation. A light yellow oil was obtained (46g, 80% yield).

The $^{13}C$—NMR showed only those absorptions necessary for the product. An ester carbonyl at 173.2 ($D_2O$ solvent, ppm downfield from TMS) was observed, and a second carbonyl at 172.9, in addition to absorptions for the methylene group of glycolic acid a 59.9ppm and those for the alkyl chain.

EXAMPLE V

Synthesis of Hexanoylacetyl Chloride

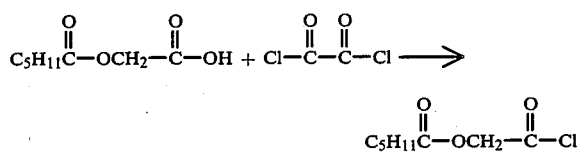

8.7g (0.05 m) of hexanoylacetic acid and 12.7 g (0.10m) of oxalyl chloride were mixed together at room temperature. The reaction was heated gradually over one hour to 50-60° C., then to 60-70° C. under aspirator pressure for one hour. The reaction mixture was diluted with 125 ml hexane, washed with 3×100 ml ice water, dried over 20 g $MgSO_4$, and roto-vapped at 50° C. to yield an oil (9.4 g, 98% yield).

EXAMPLE VI

Synthesis of Sodium, n-Hexanoyloxyacetate, p-phenylsulfonate

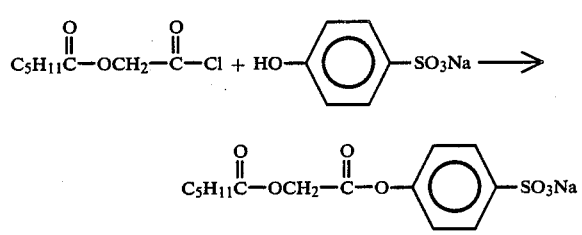

9.2 g (0.04 m) of n-hexanoyloxyacetyl chloride was added dropwise to an ice-cooled slurry of 9.0 g (0.046 m) sodium, p-phenolsulfonate (dried four hours at 110° C. in vacuo) and 5.5 g (0.045 m) triethylamine in 45 ml diglyme in a 100 ml round bottom flask fitted with a stirrer and low temperature thermometer. The reaction mixture was stirred for two hours at 0-4° C., diluted with 100 ml ethyl ether, and filtered. The white solid precipitate was triturated with 100 ml of warm isopropanol and the solid was vacuum filtered and dried overnight under house vacuum (11.5 g, 65% yield). The $^{13}C$-NMR showed only those absorptions necessary for the An ester carbonyl at 175.9 ($D_2O$ solvent, ppm downfield from TMS) was observed, and the terminal carbonyl at 169.7, in addition to those absorptions for the aromatic carbons and those the alkyl chain.

EXAMPLE VII

Synthesis of Octanoyloxyacetate, dimethyl oxime ester

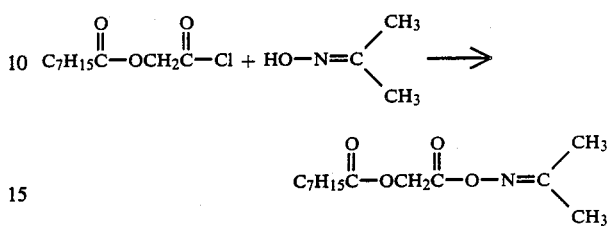

After obtaining the acid chloride of Example II, the oxime ester thereof was synthesized by following the procedure of Example I, in the co-pending application Ser. No. 928,065 (which is incorporated in its entirety herein by reference) entitled "Acyloxynitrogen Peracid Precursors," inventor Alfred G. Zielske, filed Nov. 6, 1986 same date, commonly assigned to The Clorox Company. The $^{13}C$—NMR showed only those absorptions necessary for the product. An ester carbonyl at 171 ($CDCl_3$ solvent, ppm downfield from TMS) was observed, and the terminal carbonyl at 164.6, in addition to the absorption for the oxyimide group and the alkyl chain.

EXAMPLE VIII

Synthesis of Octanoyloxyacetate, t-butyl phenol ester

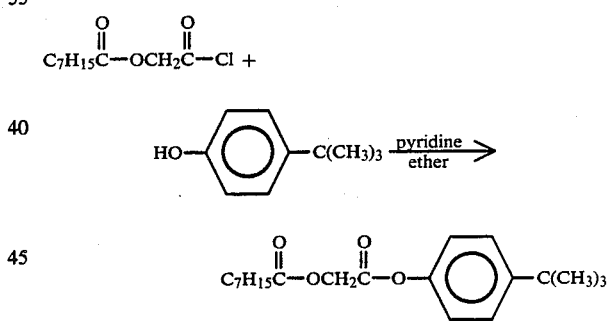

5.95 g (0.025 m) octanoyloxyacetyl chloride (which can be prepared from the steps in Examples I and II above) dissolved in about 15 ml anhydrous ethyl ether are added drop wise to a solution containing 2½]g (0.027 m) pyridine and 4.70 g (0.031 m) t-butyl phenol in about 100 ml pyridine over one half hour the solution being maintained at a temperature of 0-4° C. in an ice bath and stirred via a magnetic stir bar. The reaction was stirred at 5-10° C. for about 2 hours, filtered and then diluted to about 200 ml with ethanol. This was washed with 3 parts of 100 ml of 4 % hydrochloric acid, one part of 150 ml water, two parts of 100ml of 10% sodium carbonate solution, then dried over sodium sulfate. The product was filtered and roto-vapped to yield a yellow oil. This was chromatographed on 60 g of silica gel with 4% ethyl ether/petroleum ether distillate. The resulting product was 5.3 g of a yellow oil (8.83 g theoretical), for about 60% product yield. Product purity was determined to be about 99.9%±0.5%. IR spectroscopy show no peaks about 3000 cm$^{-1}$, and two carbonyls at 1785$^{-1}$cm and 1750$^{-1}$cm, respectively.

The $^{13}$C—NMR showed only those absorptions necessary for the product. An ester carbonyl at 173.0 (CDCl$_3$ solvent, ppm downfield from TMS) was observed, and the terminal carbonyl at 166.6, in addition to those absorptions for the aromatic carbons and those for the alkyl chain.

The $^{13}$C—NMR (CDCl$_3$, ppm downfield from TMS) showed only absorptions expected for the product. Using the numbering system shown, these assignments were made:

$$H_3C-H_2C-H_2C-H_2C-H_2C-H_2C-H_2C-\overset{O}{\overset{\|}{C}}-O-CH_2-\overset{O}{\overset{\|}{C}}-O-\underset{11\ 12}{\underset{11\ 12}{\bigcirc}}\underset{13}{\overset{15}{\underset{14}{\overset{CH_3}{\underset{|}{C}}}}}-CH_3}$$

1  2  3  4  5  6  7  8  9    10    13    15

C$_1$(14.0), C$_2$(22.6), C$_3$(24.9), C$_4$(29.0), C$_5$(31.6), C$_6$(33.8), C$_7$(173.0), C$_8$(60.5), C$_9$(166.6), C$_{10}$(148.9), C$_{11}$(126.3), C$_{12}$(120.6), C$_{13}$(147.9), C$_{14}$(34.5) and C$_{15}$(31,4).

Perhydrolysis yield of the ester (at $8.75 \times 10^{-4}$M) with hydrogen peroxide (1.75 x 10$^{-3}$M) at pH 10.5 (0.02M NaHCO$_3$/NaOH hardness) at 21° C. was 80% A.O. in 10 minutes.

EXAMPLE X

Alternate Synthesis of Acyloxyacetic Acid (acylolycolic acid)

$$R-\overset{O}{\overset{\|}{C}}-O-Na + Cl-H_2C-\overset{O}{\overset{\|}{C}}-OH \longrightarrow$$

$$R-\overset{O}{\overset{\|}{C}}-O-CH_2\overset{O}{\overset{\|}{C}}-OH$$

Following the synthesis described in Wayo, U.S. Pat. No. 2,659,697, acyloxyacetic acid (acylglycolic acid) can be synthesized by combining a neutralized carboxylic acid with chloroacetic acid.

EXAMPLE XI

Synthesis of Alkyl Esters of Acyloxyacetic Acid $$R-\overset{O}{\overset{\|}{C}}O^-Na^+ + ClCH_2\overset{O}{\overset{\|}{C}}-OH \xrightarrow{NaOAc} \quad (1)$$

$$R-\overset{O}{\overset{\|}{C}}-O-CH_2\overset{O}{\overset{\|}{C}}-OH$$

$$R-\overset{O}{\overset{\|}{C}}-O-CH_2\overset{O}{\overset{\|}{C}}-OH \xrightarrow{Cl-\overset{O}{\overset{\|}{C}}-\overset{O}{\overset{\|}{C}}-Cl} \quad (2)$$

$$R-\overset{O}{\overset{\|}{C}}-O-CH_2\overset{O}{\overset{\|}{C}}-Cl \xrightarrow{R^*OH} R-\overset{O}{\overset{\|}{C}}-O-CH_2\overset{O}{\overset{\|}{C}}-OR^*$$

Alkyl esters of acyloxyacetic acid can be prepared in accordance with the method described in Loder et al, U.S. Pat. No. 2,350,964 or Burton and Fife, "Preparation of a Series of Carbethoxymethyl Alkanoates," *J. Amer. Chem. Soc.*, vol. 74, pp 3935-6 (1952), both incorporated herein by reference, in which sodium salts of fatty acids are combined with sodium acetate and a chloroacetate. Alternatively, the acid chloride synthesis described in Examples I-III, IV-VI, above, may be followed, but alkoxy substituents will be introduced via alcohol instead of phenyl sulfonate.

EXAMPLE XIII

Benzoyl Oxyacetic Acid (a) $Cl-CH_2\overset{O}{\overset{\|}{C}}-OH + LiOH \xrightarrow{MeOH}$ (1)

m.w. = 94.5    m.w. = 41.96

$$Cl-CH_2\overset{O}{\overset{\|}{C}}-O^-Li^+ + H_2O$$

m.w. = 118.5

(b) $\bigcirc-\overset{O}{\overset{\|}{C}}-OH + LiOH \xrightarrow{MeOH}$ m.w. = 122.1

$$\bigcirc-\overset{O}{\overset{\|}{C}}-O^-Li^+ + H_2O$$

m.w. = 146.0

$Cl-CH_2\overset{O}{\overset{\|}{C}}-O^-Li^+ +$ (2)

$$\bigcirc-\overset{O}{\overset{\|}{C}}-O^-Li^+ \xrightarrow[(2)\ H^+(aq.)]{(1)\ DMF/D}$$

$$\bigcirc-\overset{O}{\overset{\|}{C}}-O-CH_2\overset{O}{\overset{\|}{C}}-OH + 2\ LiCl$$

m.w. = 180.15

(1) Salt Formation (a) Lithium Chloroacetate: 9.45 g (0.10 m) chloroacetic acid was dissolved in 30 ml methanol. 4.2 g lithium hydroxide (0.10 m) was dissolved in 50 ml of methanol. The two methanol solutions were combined and rotary evaporated to a white powder (wt=13 g).

(b) Lithium Benzoate: 25.6 g (0.21 m) benzoic acid was dissolved in 25 ml methanol. 8.4 g (0.20 m) lithium hydroxide was dissolved in 75 ml methanol. The two methanol solutions were combined and rotary evaporated to a white powder. wt=31 g.

(2) Benzoyloxy Acetic Acid 13 g lithium chloroacetate (0.10 m) and 17.6 g lithium benzoate (0.10 m) were combined in a 250 ml R.b. flask with 50 ml DMF. This was heated on an oil bath to 110°-120° C. with magnetic stirring for 3 hrs. (The solution at first was clear, but after 2-3 hrs. a white precipitate formed).

The reaction was cooled to 100° C. and solvent distilled off under high vacuum, leaving a pasty residue which was dissolved in 150 of 4% HCl, which was extracted three times with 100 ml ethyl ether. The combined ether layer was dried over Na$_2$SO$_4$, filtered and rotary evaporated to a paste weighing 14 g.

The product paste was chromatographed on 125 g silica gel in 33% ethyl ether/66% petroleum ether. Two cuts were made: Fraction I (1st 600 ml) which was impure product and Fraction II (next 400 ml) which contained 2.2 g of one spot material as product. Fraction I (13 g) was rechromatographed on 124 g silica gel (25/75 ethyl ether/pet. ether). 10 Fifty ml fractions were taken. Fractions 6 through 10 continued 3.2 g of pure product. Combined product 5.4 g (30% yield) (mp=107° C.).

The $^{13}$C—NMR (D$_2$O, ppm downfield from TMS) showed only absorptions expected for the product. Using the numbering system shown, these assignments were made:

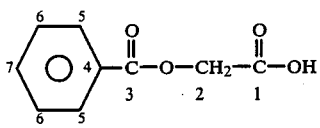

C$_1$(173.1), C$_2$(60.7), C$_3$(166.1), C$_4$(129.1), C$_5$(130), C$_6$(128 5), and C$_7$(133.5).

EXAMPLE XIV

Benzoyl oxyacetate, Phenol Sulfonate Ester

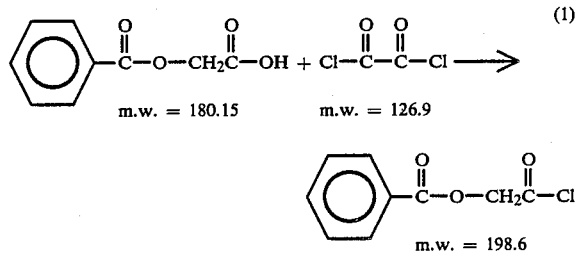

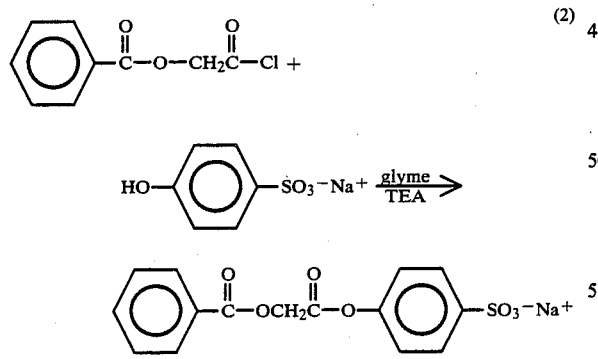

(1) Benzoyloxyacetyl chloride 4.1 g (0.023 m) Benzoyloxy acetic acid (as synthesized in Example XIII) was combined with 2.96 ml (4.3 g, 0.032 m) oxalyl chloride in 50 ml petroleum ether. This was stirred under a CaSO$_4$ drying tube for 5 hrs., at which time 2.0 ml more oxalyl chloride and 50 ml chloroform were added. The reaction was stirred overnight.

Excess oxalyl chloride was removed at aspirator pressure by heating to 55° C. on an oil bath. The reaction was diluted with ml hexane (a white precipitate formed which was filtered off). The hexane layer was washed with 5×50 ml ice cold H$_2$O. The hexane layer was dried over 30 g Na$_6$SO$_4$, filtered and rotary evaporated to an oil wt=4.0 g (4.6 g theoretical) (IR: one carbonyl at 18/5 cm$^{-1}$, another at 1740 cm$^{-1}$). The oil was used as in in reaction (2), below.

(2) Benzoyloxy Acetic Acid, Phenol Sulfonate Ester

The 4.0 g (0.020 m) of acid chloride from (1) above was combined in a 250 ml R.b. flask with 4.9 g 0.025 m) dried phenol sulfonate and 30 ml glyme. This slurry was stirred on an ice-water bath with a magnetic stir bar and 3.5 ml ( 2.5 g, 0.025 m) triethylamine (TEA) was added dropwise. Over the TEA addition the reaction thickened and turned yellow. The reaction was stirred overnight following the addition of 30 ml glyme.

50 ml ethyl ether was added with stirring and the reaction was filtered on a C-Frit. The filter was washed with 2×40 ml ethyl ether. The crude product filtrate was re-crystallized from 30 ml boiling IPA (70% vol)-/water (30% vol). Cooling, filtration and vacuum drying (3hrs, 70° C.) gave 2.8 g of white powder, which was determined to be 78% product by HPLC, saponification, and NMR ($^{13}$C)

$^{13}$C—NMR confirms the desired product, phenol sulfonate and benzyl oxy acetic acid. Qualitative HPLC observes four peaks under the conditions of analysis described. The purity value calculated from ester content assumes that all ester groups are from the desired compound.

The $^{13}$C—NMR (D$_2$O, ppm downfield from TMS) showed only absorptions expected for the product. Using the numbering system shown, these assignments were made:

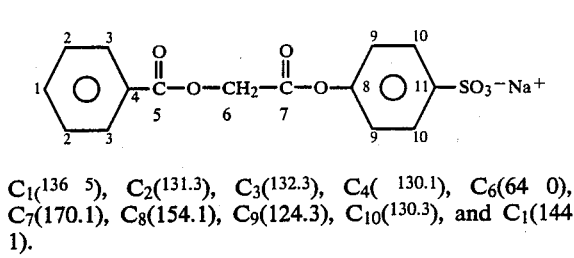

C$_1$($^{136}$ 5), C$_2$($^{131.3}$), C$_3$($^{132.3}$), C$_4$($^{130.1}$), C$_6$(64 0), C$_7$(170.1), C$_8$(154.1), C$_9$(124.3), C$_{10}$($^{130.3}$), and C$_1$(144 1).

EXAMPLE XV

Octanoyloxy Acetic/Acetic Acid Mixed Anhydride

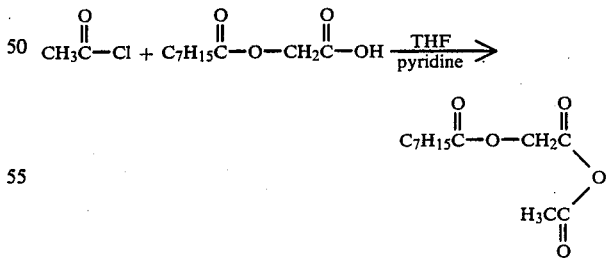

Procedure: One equivalent of octanoyloxy acetic acid (OOAA) and one equivalent of pyridine are charged into a reaction vessel with THF (enough to keep the reaction fluid over its course). The mechanically stirred reaction is begun on the slow dropwise addition of one equivalent of acetyl chloride and stirring for approximately 1 hr. after addition. The pyridine hydrochloride is isolated by filtration and the solvent removed on a rotary evaporator at low (30–35° C.)

temperature leaving behind the mixed anydride, yield should be nearly quantitative.

EXAMPLE XVI

In Situ Generation of Octanoyloxyperacetic Acid $$CH_3(CH_2)_6-\overset{O}{\underset{\|}{C}}-OCH_2\overset{O}{\underset{\|}{C}}-O-\phantom{x}\!\!\!\!\!\!\!\!\!\!\!\!\!\!\!\!\bigcirc\!\!\!\!\!\!\!\!\!\!\!\!\!\!\!\!\phantom{x}-SO_3^-Na^+ \xrightarrow[pH\ 10.5]{OOH^-}$$

$$CH_3(CH_2)_6-\overset{O}{\underset{\|}{C}}-OCH_2\overset{O}{\underset{\|}{C}}-O-OH\ +\ -O-\phantom{x}\!\!\!\!\!\!\!\!\!\!\!\!\!\!\!\!\bigcirc\!\!\!\!\!\!\!\!\!\!\!\!\!\!\!\!\phantom{x}-SO_3^-\ +\ Na^+$$
(I)

$$OOH^-\ \Big|\ pH\ 10.5$$

$$CH_3(CH_2)_6-\overset{O}{\underset{\|}{C}}-O-OH\ +\ HO-CH_2\overset{O}{\underset{\|}{C}}-O-OH$$
(II)                    (III)

Octanoyloxy acetic acid, phenyl sulfonate ester (also known as octanoylgycolate, phenyl sulfonate ester), as synthesized in the manner of Example III, above, was treated with perhydroxide anion and high performance liquid chromatography ("HPLC") was used to determine the presence of the thus generated peracids, using an electrochemical detector which detects only peracids.

In the EC chromatogram, perglycolic acid (III) came off first at 1.55 minutes, then peroctanoic acid (II) at 10.88 minutes and finally, octanoyloxyperacetic acid (peroctanoyloxyglycolic acid) (I) at 17.03 minutes. In this assay, the following observed concentrations were measured: about 0.86 mM perglycolic acid, about 0.86 mM peroctanoic acid, and about 2.45 mM octanoyloxyglycolic acid. UV chromatogram ascertained the presence of about 0.6 mM octanoic acid and about 1.69 mM octanoyloxyacetic acid. About 4.0 mM total A.O. and about 4.17 mM peracid were found.

EXAMPLE XVII

The acyloxyacetic acid esters give excellent stain removal performance. Their performance is comparable to that of fatty acid based peracids which have been reported in the patent literature to be very efficient surface active bleaching agents. TABLE V below discloses the crystal violet stain removal data for the inventive precursors.

TABLE V

| Compound | % SR(E) Crystal Violet |
|---|---|
| $H_2O_2$ | 35 |
| $CH_3(CH_2)_6\overset{O}{\underset{\|}{C}}-OOH$ | 89 |
| $C_5H_{11}\overset{O}{\underset{\|}{C}}-OCH_2\overset{O}{\underset{\|}{C}}-O-\phantom{x}\!\!\!\!\!\!\!\!\bigcirc\!\!\!\!\!\!\!\!\phantom{x}-SO_3^-Na^+$ | 85 |

TABLE V-continued

| Compound | % SR(E) Crystal Violet |
|---|---|
|  | 86 |
| $C_7H_{15}\overset{O}{\underset{\|}{C}}-OCH_2\overset{O}{\underset{\|}{C}}-O-\phantom{x}\!\!\!\!\!\!\!\!\bigcirc\!\!\!\!\!\!\!\!\phantom{x}-SO_3^-Na^+$ | 69 |
| $C_9H_{19}\overset{O}{\underset{\|}{C}}-OCH_2\overset{O}{\underset{\|}{C}}-O-\phantom{x}\!\!\!\!\!\!\!\!\bigcirc\!\!\!\!\!\!\!\!\phantom{x}-SO_3^-Na^+$ | 80 |
| $C_7H_{15}\overset{O}{\underset{\|}{C}}-OCH_2\overset{O}{\underset{\|}{C}}-O-\phantom{x}\!\!\!\!\!\!\!\!\bigcirc\!\!\!\!\!\!\!\!\phantom{x}-OH$ | 49 |
| $C_7H_{15}\overset{O}{\underset{\|}{C}}-OCH_2\overset{O}{\underset{\|}{C}}-OCH_3$ |  |

*pH 10.5, 5 min, 70° F., 2:1 molar ratio peroxide: activator, Pluronic L63 surfactant (.1 wt %)

What is claimed is:

1. A peracid of the structure $$R-\overset{O}{\underset{\|}{C}}-O-\overset{R'}{\underset{R''}{\overset{|}{C}}}-\overset{O}{\underset{\|}{C}}-OOH,$$

wherein R is $C_{1-20}$ linear or branched alkyl, alkoxylated alkyl, cycloalkyl, aryl, alkyl substituted aryl; and R' and R'' are independently H, $C_{1-20}$ alkyl, aryl, $C_{1-20}$ alkyl, aryl, $C_{1-20}$ alkylaryl, aryl substituted with OH, $CO_2$ or $SO_3$, and $NR^{a+}{}_3$, wherein $R^a$ is $C_{1-30}$ alkyl.

2. The peracid of claim 1 wherein R is $C_{1-20}$ alkyl or aryl.

3. The peracid of claim 2 having the structure $$R-\overset{O}{\underset{\|}{C}}-O-CH_2-\overset{O}{\underset{\|}{C}}-O-OH,$$

wherein R is $C_{4-17}$ alkyl, or aryl.

4. The peracid of claim 3 which is octanoyloxyperacetic acid.

5. The peracid of claim 3 which is benzoyloxyperacetic acid.

6. The alkali metal and alkaline earth salts of the peracid of claim 1.

7. A peracid precursor of the structure

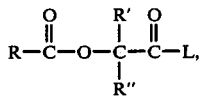

wherein R is a $C_{1-20}$ straight or branched chain, alkyl, alkoxylated alkyl, cycloalkyl, aryl, or alkyl substituted aryl, R' and R" are independently H, $C_{1-20}$ alkyl, aryl, $C_{1-20}$ alkylaryl, aryl substituted with OH, $SO_3$ or $CO_2$, and $NR_3^{a+}$, wherein $R^a$ is $C_{1-30}$ alkyl, and L is a leaving group selected from:

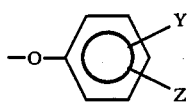

wherein Y and Z are individually H, $SO_3M$, $CO_2M$, $SO_4M$, OH, halogen, $-OR^2$, $R^3$, or $NR_3^4X$, wherein M is an alkali metal or alkaline earth metal counterion, $R^2$ of $-OR^2$ is $C_{1-20}$ alkyl, $R^3$ is $C_{1-6}$ alkyl, $R^4$ of $NR_3^4$ is $C_{1-30}$ alkyl, X is a counterpart ion, and Y and Z can be the same or different;

(b) $-ONR^6$, wherein $R^6$ comprises at least one carbon which is singly or doubly bonded directly to N; and (c)

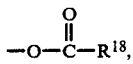

wherein $R^{18}$ is $C_{1-10}$ alkyl.

8. The precursor of claim 7 with the structure

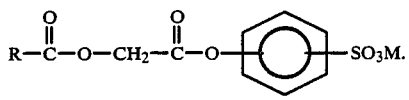

9. The precursor of claim 7 with the structure

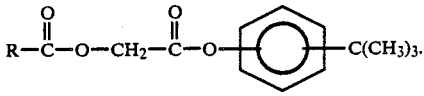

10. The precursor of claim 7 with the structure

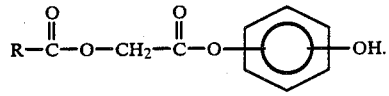

11. The precursor of claim 7 with the structure

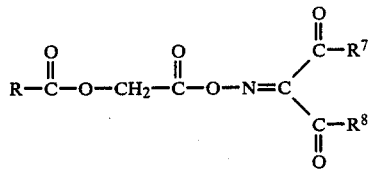

wherein $R^7$ and $R^8$ are each H or $C_{1-20}$alkyl, aryl, alkylaryl or mixtures thereof, and $R^7$ and $R^8$ can be the same or different, but at least one of $R^7$ or $R^8$ is not H.

12. The precursor of claim 7 with the structure

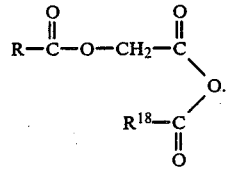

13. The peracid of claim 3 which is heptanoyloxyperacetic acid.

14. The peracid of claim 3 which is nonanoyloxyperacetic acid.

15. The peracid of claim 3 which is decanoyloxyperacetic acid.

16. The precursor of claim 8 which is hexanoyloxyacetyl phenyl sulfonate.

17. The precursor of claim 8 which is heptanoyloxyacetyl phenyl sulfonate.

18. The precursor of claim 8 which is octanoyloxyacetyl phenyl sulfonate.

19. The precursor of claim 8 which is nonanoyloxyacetyl phenyl sulfonate.

20. The precursor of claim 8 which is decanoyloxyacetyl phenyl sulfonate.

* * * * *

UNITED STATES PATENT AND TRADEMARK OFFICE
CERTIFICATE OF CORRECTION

PATENT NO. : 4,959,187
DATED : September 25, 1990
INVENTOR(S) : Ronald A. Fong et al.

It is certified that error appears in the above-identified patent and that said Letters Patent is hereby corrected as shown below:

Column 6, line 6, delete the number "32" and insert -- = --.

Column 7, line 16, change "esters. Possess" to reach --- esters possess ---

Column 7, line 16, delete punctuation mark (.) between the words "reactivity" and "yields" and insert -- , --".

Column 10, above first paragraph of text, insert --- (B) Halides ---

Column 13, line 33, replace the word "it" with --- if ---

Column 16, line 5, insert --- $R^{19}$ --- at the beginning of the line

Column 16, line 6, delete "$R^{19}$ is"

Column 15, lines 44-45, delete the phrase "on page 22, line 1.5"

UNITED STATES PATENT AND TRADEMARK OFFICE
CERTIFICATE OF CORRECTION

PATENT NO. : 4,959,187
DATED : September 25, 1990
INVENTOR(S) : Ronald A. Fong et al.

Page 2 of 2

It is certified that error appears in the above-identified patent and that said Letters Patent is hereby corrected as shown below:

Column 20, line 51, delete the word "dine" and insert the word --- pyridine ---

Column 22, line 28 should read --- slurry over 1/2 hour. The reaction becomes very thick during this time ---

Column 24, line 24, delete the phrase "same date"

Column 25, line 29, the word "Acyloxvacetic" should read --- Acyloxyacetic"

Signed and Sealed this

Twenty-ninth Day of June, 1993

Attest:

MICHAEL K. KIRK

*Attesting Officer*   Acting Commissioner of Patents and Trademarks